United States Patent [19]
Sheets

[11] Patent Number: 4,647,300
[45] Date of Patent: Mar. 3, 1987

[54] METHODS OF MAKING CUTTING IMPLEMENTS AND RESULTING PRODUCTS

[76] Inventor: Payson D. Sheets, 520 Marine St., Boulder, Colo. 80302

[21] Appl. No.: 572,175

[22] Filed: Jan. 18, 1984

Related U.S. Application Data

[63] Continuation-in-part of Ser. No. 301,953, Sep. 14, 1981, abandoned.

[51] Int. Cl.$^4$ .............................................. C03B 33/00
[52] U.S. Cl. ........................................ 65/105; 65/112; 128/314; 128/315; 128/339; 225/96.5
[58] Field of Search ................. 65/105, 112; 225/96.5; 128/314, 315, 339

[56] References Cited

U.S. PATENT DOCUMENTS 1,551,351  8/1925  Wayringer ............................ 65/105

OTHER PUBLICATIONS

The Encyclopedia Americana, vol. 25, pp. 746, 747, Oct. 16, 1978.
Washington Post, 1-1-81—Metro Section, "New Use for Ancient Tool".
Science 81, vol. 2, #1, Sep. 1981, pp. 79-80, "A Touch of Glass", J. Schwarz.
OMNI, vol. 4, #4, 1-82—p. 35, Stone Age Scalpels.
Science Digest, vol. 90, #10, 10-82, p. 91, Glass Scalpel Outcuts Steel.
Science News, vol. 124, #6, 8-6-83—p. 93, "Glass Blades".
GEO, vol. 5, #11, 11-83, p. 116, "New Surgical Blades are Based on Ancient Maya Knives".
American Medical News, American Medical Assoc., 11-2-84, pp. 1, 21-24, "New Revolution in the Making".
New Medical Science, 12-84, vol. 1, No. 1, pp. 7, 14, 15, "Obsidian Blades The Cutting Edge of Scalpel Technology".
Breakthrough, The Newsletter of Innovation, by Boardroom Reports, 2-15-85, vol. III, No. 4, p. 3.

Primary Examiner—Arthur Kellogg
Attorney, Agent, or Firm—Donald W. Margolis

[57] ABSTRACT

The invention comprises a method of forming cutting blades from solid vitreous material by first placing a mass of molten material into a mold having at least one indentation to cause a ridge to form adjacent to a first surface in the material, cooling the molten material at a rate to preclude internal stresses or other inhomogeneity in the solid material, forming a second substantially flat surface intersecting the ridge area and finally directing fracturing pressure in a controlled direction of force into the material at the second surface in the vicinity of the said ridge in a direction substantially parallel to the first surface whereby a cutting implement is sheared off of the said material.

12 Claims, 20 Drawing Figures

METHODS OF MAKING CUTTING IMPLEMENTS AND RESULTING PRODUCTS

This is a continuation-in-part of application Ser. No. 301,953, filed Sept. 14, 1981 now abandoned.

BACKGROUND OF THE INVENTION

1. Field of the Invention

This invention relates to methods of making cutting blades and to the resulting blades; and more particularly it relates to methods of making extremely sharp surgical cutting implements out of vitreous materials and to the resulting surgical blades.

2. Prior Art

Many types of cutting blades are available to today's surgeons, but only a limited number of methods are used for manufacturing such blades. The sharper the blade, the narrower the incision that it will make, and the less pressure will be required to use it. As a result, the sharper the blade that is used, the less tissue trauma and bruising will result from each incision, and healing of the incision will be facilitated with less resulting scarring. Steel blades are presently most often used as scalpels for surgical procedures because of their durability, strength and relative sharpness, availability, moderate price, and also due to tradition, training and lack of alternatives. Steel cutting implements are made as they have been for decades using rolling or other flattening techniques, followed by grinding and honing. Nonetheless, scanning electron photomicrography demonstrates that many steel scalpels are surprisingly dull with edge rounding being seen at magnifications as low as about 30 to 100 times. By comparison, even ordinary steel razor blades are found to be about twice as sharp as commercially available disposable surgical scalpels. For this reason razor blade fragments have often been used for delicate surgical procedures, including eye surgery.

Honed diamond blades are also used as scalpels when fine incisions and delicate procedures are required. While photomicrographs show that diamond blades are substantially sharper than steel scalpels, having edge radii on the order of 100 angstroms, they are also more expensive and time consuming to produce than steel blades. U.S. Pat. No. 3,060,781 to Villalobos teaches one diamond cutter's approach to producing such a sharp diamond cutting tool. Methods of making honed aluminum oxide blades are taught by U.S. Pat. No. 3,543,402 to Seager.

Other non-metallic blades of superior sharpness have been formed from natural volcanic glass, such as obsidian, or from other vitreous, ceramic, or microcrystalline materials, using controlled fracturing methods of manufacture. In controlled fracturing methods, pressure is selectively applied to a block or a portion of a block of the material which has been selected for its shape, and fracturing of the material will then normally occur substantially along predictable angles from the vectors of applied force. When such force is applied to many naturally occurring vitreous or ceramic materials, such fracturing techniques will produce a much sharper edge than does steel honing or even diamond polishing because the edge produced by such fracturing is only a few molecules thick. However, traditional fracturing methods applied to traditional naturally occurring materials have not been applicable to the controlled production of cutting implements. This is due to the fact that cores or blocks of naturally occurring vitreous material, such as obsidian, will substantially always contain structural or molecular orientations (phenocrysts), imbedded stress fields caused by irregular cooling of the material at its time of formation, imperfections and inclusions (xenoliths), all of which are difficult to detect. These structural characteristics of naturally occurring vitreous materials will almost always cause fracturing along unpredictable lines or planes to produce cutting implements of unpredictable size and shape. Consequently, it is difficult to produce one or more blades of desired predetermined dimensions and configurations from naturally occurring vitreous materials. It is even more difficult to produce a series of blades which are all of predetermined size and shape from naturally occurring vitreous materials. While an occasional blade of desired dimension and configuration may be produced from natural vitreous material using standard fracturing techniques, much time and effort, and much of the core material may be wasted in this inefficient process.

Some mechanical processes for producing cutting implements from artificially produced vitreous material, such as glass, are known. Prior art which discloses methods for forming cutting edges from glass includes U.S. Pat. No. 3,207,398 to Forsstrom, et al. for a device for cutting glass plates to produce sharp edges; U.S. Pat. No. 3,819,096 to Pyper for glass knives; and U.S. Pat. No. 3,908,878 to Blum for microtome cutting edges. These, and all other prior art methods for forming cutting edges from artificially produced vitreous material, of which applicant is aware, involve the steps of scoring a glass block of given thickness, followed by force and pressure and fracturing of the block along the scored lines. Tafapolsky, et al. in U.S. Pat. No. 3,834,265 disclose techniques for producing ceramic (sapphire) razor blades and knives using microtome techniques followed by chemical sharpening. Glass and ceramic cutting implements which are produced using these prior art techniques are limited in length to the thickness of the glass block, can carry only one cutting edge per segment, cannot be produced in a manner which allows them to have a pointed or tapered end, and are always straight and cannot be produced with a curved cutting edge.

Honed glass razor blades may be produced according to U.S. Pat. No. 2,555,214 by Wallach, et al. which teaches a method of producing glass razor blades by the tedious steps of grinding followed by etching in extremely dangerous and toxic hydrofluoric acid. Again, glass cutting implements produced using this technique will carry only one cutting edge per segment, cannot be produced in a manner which allows them to have a pointed or tapered end, and are always straight and cannot be produced with a curved cutting edge.

SUMMARY OF INVENTION

The method of the present invention provides methods of making cutting blades from artificially produced vitreous materials, which methods substantially eliminate the element of chance and unpredictability as to the size and configuration of the resulting blade. As a result the method of the present invention provides for the economical manufacture of vitreous cutting blades which may be of almost any standard or desired specific size and configuration, and of sharpness suitable for even the most delicate surgical procedures. In preferred embodiments a plurality of vitreous cutting blades of substantially the same size, configuration and sharpness can be produced from a single core of starting material and from a series of similar cores.

The method of the present invention will involve the substitution of a core of substantially pure manufactured vitreous material, such as glass, for the prior art natural vitreous or mineral material. This pure manufactured vitreous material will be substantially free of structural imperfections, molecular orientations, stress fields, zones of weakness, and cleavage, and inclusions which might otherwise disrupt the anticipated and desired fracturing of the core. Furthermore, in preferred embodiments, the core will have a molded shape for ease in producing one or more blades of predetermined and controlled size and configuration.

In accordance with the practice of the method of the present invention, cutting instruments composed of glass or other vitreous material will be formed from material which is substantially free of structural imperfections, molecular orientations, stress fields, zones of weakness and cleavage, and inclusions. Typically, such resulting blades will be comprised of a body of elongated slender shape having a proximal or holding end, a distal end and a pair of opposed sharp edges. In certain preferred embodiments, the body of the blade can be made to taper or curve forwardly and/or sidewardly from the proximal end, and/or terminate in a relatively sharp tapered angle at the distal end. The preferred form of starting core will carry one or more convex or angled ridges which will substantially define the morphology of the resulting implement by directing the fracture path and by defining the lateral width of the resulting blade. In a similar manner, the dorsal surface of the resulting blade will be longitudinally curved or planar between the proximal and distal ends, as was the curve or plane of the core body from which it was fractured. Blades produced by the practice of the present invention will have two intersecting side edges between their dorsal and ventral surfaces. One or both edges will define extremely sharp, uniform, continuous cutting edges, having edge radii usually on the order of about 20 to about 60 angstroms, but almost always less than 300 angstroms, which edges will extend for substantially the entire edge length of the blade body.

In the formation of such cutting or surgical implements, the starting block or core material will be composed of an amorphous vitreous material substantially free of structural imperfections, molecular orientations, stress fields, zones of weakness or cleavage, and inclusions. In preferred embodiments the core material will be molded to a desired shape from hot viscous vitreous material and will have at least one ridge or other discontinuity which will define a cleavable portion and configuration. By selecting the height of the core, the width and configuration of the ridge or discontinuity, and the point and angle of applied force, the size and configuration of the resulting blade can be substantially predetermined using controlled rate and force vector pressure fracturing techniques.

In preferred methods of the present invention, each starting core will have a plurality of substantially uniform fluted surfaces defining ridges which are curved or angled in cross-section and which extend longitudinally along the face of the core approximately parallel to one another. Each ridge will be separated from the adjacent longitudinal ridge and be bracketted by a pair of valleys formed in the face of the core parallel to and between each pair of adjacent ridges.

In the practice of making blades according to the present invention, continuous and increasing pressure will be applied with a relatively sharp-edged tool from a point proximate to a proximal end of a ridge and bracketted by an adjacent pair of valleys. The end of the core to which pressure will be applied is called the "platform". In preferred embodiments the platform will be very flat in order to avoid uncontrolled distribution of force. Such a flat platform may be provided by cutting the core with a diamond saw.

The pressure vector will initially be applied to the platform in a controlled direction of force into the core material, usually adjacent to and in a direction substantially parallel to the longitudinal direction of the proximal end of the ridge and its adjacent valleys. A second different, but lesser vector will then be added to the first vector so that the induced stress field in the core will be shifted until it is substantially parallel with the face of the adjacent ridge. When the elastic limit of the core material is exceeded this combination of pressure and vectors will cause a shard of vitreous material to be cleaved from the core, the shard having its approximate lateral dimension equivalent to the distance between the bracketting valleys, while its height will normally be controlled by the height of the core. It will be appreciated that heights less than the height of the core can be intentionally achieved, but that this is different than height termination of the type which occurs in the practice of the prior art due to structural imperfection.

Where the height and shape of the block of starting core material is appropriately designed, cutting implements of predetermined length and width dimensions can be formed using this technique. The controlled application of continuous force first in a direction parallel to a ridge, and then in a direction at an angle out from the face of the core will result in various preferred forms of cutting implements, as described in more detail hereinbelow. In virtually every instance the cutting implement will have an elongated body with a pair of extremely sharp cutting edges extending along opposite sides at the intersection of the dorsal and ventral surfaces of the implement.

Where the starting block material has a plurality of equally spaced and similarly shaped ridges and valleys, a series of substantially identical cutting implements can be formed from that core by the practice of the method of the present invention. This will be accomplished by the successive application of force, in the manner described, along the top of each successive ridge which is bracketted by a pair of adjacent valleys. In one preferred embodiment, in which the starting block material has a plurality of equally spaced ridges and valleys, the controlled application of force to a successive series of ridges, and the fracturing of cutting blades therefrom, will result in the formation of a new core face on which there will be a series of secondary ridges and valleys from which additional cutting implements can be easily and economically formed from the same core material and in the same manner, by the practice of the method of the present invention.

In the preferred method of practicing the present invention, the force applied in fracturing the cutting implement from the core of material will be of the "static loading" kind in which continuous, gradually increasing pressure on the platform in a direction substantially parallel to the core face is first applied. The initial application of perpendicular pressure to the core platform by a solid tool will generate stress fields in the core in a cone of about 45° to the platform at which pressure is being applied, or at about 135° to a pressure exerting implement which is perpendicular to the core surface. The subsequent gradual loading of the second force vector will cause the stress field to be shifted substantially parallel to the to-be-cleaved surface. This will cause the shard fractured from the core to have a substantially constant thickness between its medial dorsal and ventral surfaces. Such static-loading pressure may be applied in any number of ways, for example with a manual punch, with a hydraulic press or with other suitable manually manipulated mechanical systems. In preferred embodiments a manually operated machine is used to exert pressure on the platform in both the initial and the second vector, as set forth in greater detail hereinbelow.

In the practice of the present invention, it is necessary to avoid scoring prior to fracturing and to perform the fracturing operation along a predetermined plane without distortion or interruption due to any structural imperfections, molecular orientations, stress fields, zones of weakness and cleavage, or inclusions in the core material.

It is therefore an object of the present invention to provide for novel and improved methods of making cutting implements out of a core of vitreous material which is substantially free of structural imperfections, molecular orientations, stress fields, zones of weakness and cleavage, and inclusions.

It is another object of the present invention to provide for rapid, safe and economical methods of forming surgical cutting implements composed of a vitreous material; substantially free of structural imperfections, molecular orientations, stress fields, zones of weakness and cleavage, and inclusions.

It is another object of the present invention to provide for rapid, safe and economical methods of forming surgical cutting implements composed of a vitreous material; and further wherein a series of cutting implements may be formed out of a common core of vitreous material in an extremely efficient and reliable manner.

It is further object of the present invention to provide for novel and improved cutting blades characterized in particular by being composed of and formed from vitreous material which is substantially free of structural imperfections, molecular orientations, stress fields, zones of weakness and cleavage, and inclusions, which material is fractured from a core of such material in such a manner as to form an elongated body with one or more extremely sharp cutting edges having useful application in the field of surgery; and further wherein when used for surgery the edges formed by such fracturing will make a narrower incision and require less pressure than does a standard metal scalpel, with the result that there will be less trauma, bruising, tearing and translocation to the tissue, and as a further result of which healing of such incisions will be facilitated with reduced scarring.

It is further object of the present invention to provide for a novel and improved method of manufacturing surgical cutting implements from a common core of vitreous material which requires a minimum number of steps and which allows closely controlled size and shape fracturing of one implement, or of a plurality of such implements from a common core of material.

It is an additional object of the present invention to provide for methods of manufacturing a series or plurality of substantially identical surgical cutting implements from a common core of material by the application of controlled fracturing through the core in such a way as to produce a surgical cutting implement having one or more sharp cutting edges.

These and other objects of the present invention will become apparent to those skilled in the art from the following detailed description, showing the novel construction, combination, and arrangement of parts as herein described, and more particularly defined by the appended claims, it being understood that such changes in the precise embodiments of the herein disclosed invention are meant to be included as come within the scope of the claims except insofar as precluded by the prior art.

For a fuller understanding of the nature and objects of the invention, reference should be had to the following detailed description taken in connection with the accompanying drawing.

BRIEF DESCRIPTION OF THE DRAWINGS

The accompanying drawings illustrate complete preferred embodiments of the present invention according to the best modes presently conceived for the practical application of the principles thereof, and in which:

FIG. 19 is a cross-sectional view taken along line 19—19 of the cutting implement illustrated in FIG. 18.

DETAILED DESCRIPTION OF THE PREFERRED EMBODIMENTS

Figure 1:
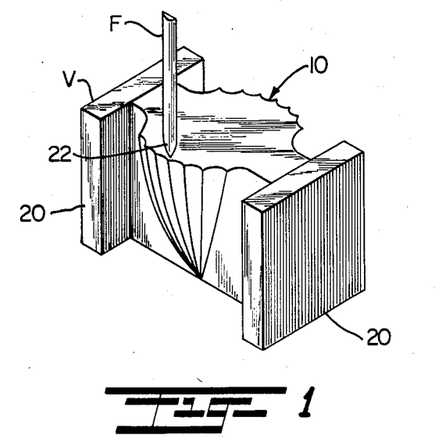
FIG. 1 is a perspective view illustrating the method of fracturing cutting implements from a secured preformed core.
Figure 2:
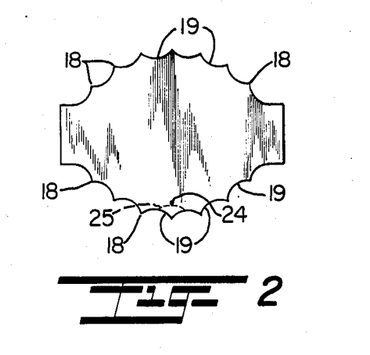
FIG. 2 is a top plan view of one preferred form of unsecured core material of the type shown in FIG. 1.
Figure 3:
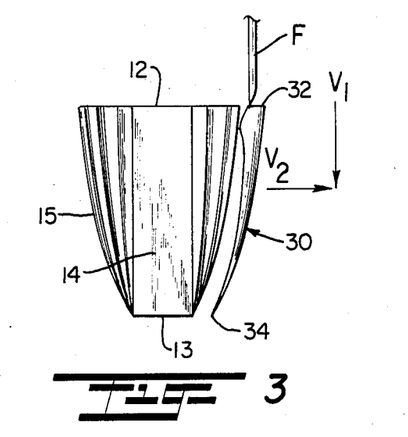
FIG. 3 is a side view in elevation of the preferred form of core material shown in FIGS. 1 and 2, illustrating a cutting implement which has been fractured and removed from it.
Figure 4:
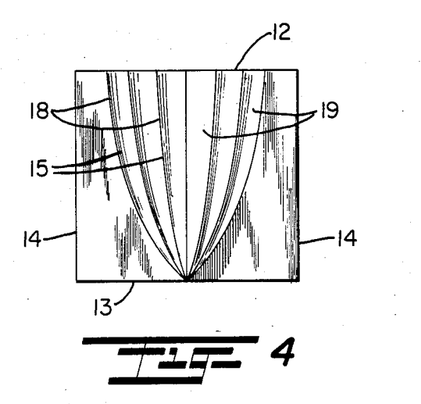
FIG. 4 is a front view in elevation of the preferred form of core material shown in FIGS. 2 and 3.

Referring in more detail to the drawings, there is illustrated in FIG. 1 a preferred method of forming cutting implements from a preformed core of material, the core material being illustrated in more detail in FIGS. 2 to 4. The core material 10 preferably will be composed of a vitreous material, such as glass which is substantially free of structural imperfections, molecular orientations, zones of weakness and cleavage, and inclusions, and which will be shaped by molding. For example, a silicate alkali or alkaline earth compound, with suitable additives and/or colorants will be melted or heated to a semi-plastic state, poured or placed into a suitable mold, and then cooled uniformly in all directions at a calibrated rate to form a solid block as designated at 10. Flat platform top 12 may be subsequently formed by sawing with a diamond saw, for example. Core 10 will also have a bottom surface 13, opposed substantially flat side surfaces 14, and opposed front and rear fluted surfaces 15. Front and rear surfaces 15 each carry a plurality of individually concave fluted surfaces which are formed between opposed sides 14. From a consideration of FIGS. 2 to 4, the fluted surfaces formed in this embodiment along each face will be seen to consist of a plurality of initially parallel relatively sharp-edged ridges 18 extending in substantially the same direction and then converging as they taper downwardly toward one another from upper surface 12 to bottom surface 13. Each ridge 18 will be separated from the next adjacent ridge 18 by a valley 19 which will be initially parallel to the ridge and which will then correspondingly taper downwardly towards one another as do ridges 18. The profile between each valley 19 and its two adjacent ridges 18 will be concave in cross-section.

Although dimensions will not be particularly critical in the practice of the present invention, a typical block or core of material 10 may be on the order of 3 inches (7.5 cm) in height, 1.5 inches (3.75 cm) in width between opposite side surfaces 14, and 4 inches (10 cm) in depth or length between outermost ridges 18 at the midpoint front and rear surfaces 15. The depth of the valleys 19 may be on the order of about one to three millimeters, with the width of the ridges at the widest point being on the order of two to three millimeters. In the practice of the method of the present invention, the height of the core, and the sizing and spacing between the ridges and valleys will largely be selected in accordance with the size of the cutting implement which it will be desired to form out of the core, as will become more readily apparent from the method of manufacturing the cutting blades as hereinafter described. For example, core heights of as small as 1 mm to as long as 20 cm will be feasible in use to produce cutting implements of similar length, while even shorter and taller cores will be feasible, if required. In most instances, blades having a length of from about 3 mm to about 10 cm will be produced, from cores of about the same height, with the majority of those blades being from about 1 cm to about 6 cm in length.

Referring in more detail to FIG. 1, in the practice of the method of the present invention core material 10 will be placed in a vise of conventional construction having a pair of pressure plates or jaws 20 between which opposite flat sides 14 of the material 10 will be positioned in a manner such that platform surface 12 will be accessible. Pressure plates 20 will be drawn together against sides 14 of core 10 so as to firmly support and position core material 10 for the fracturing operation of the present invention. A fracturing tool F, as shown in FIGS. 1 and 3 may take the form of a punch having a relatively sharp tapered end 22. Sharp end 22 of punch F will be placed into engagement with platform surface 12 of core 10 radially behind a ridge 18. The exact point of engagement, such as, illustrated at the imaginary pressure point 24 in FIG. 2, will be on the order of the depth of valley 19, in this case about one to three millimeters away from the dorsal edge of the ridge 18 and substantially midway between adjacent valleys 19. With this form of starting core material 10, the primary or initial vector of static pressure force V which will be exerted on platform surface 12 of core 10 in initiating a fracture in the core material will be in a substantially vertically downward direction or substantially parallel to the top of ridge 18. Once static pressure fracturing is initiated, such as by the application of continuous vertical pressure by punch F to platform 12, the vector or direction of force will be subsequently modified so as to be in a direction more nearly normal to and outwardly away from fluted surface 15 from which the cutting implement will be formed. Thus, the primary vector of force will first be in a direction which is substantially parallel to the longitudinal direction of extension of ridge 18, while a secondary vector of force V will then be applied in a direction more nearly transverse to and away from the direction of extension of ridge 18. Application of increasing pressure will cause the fracture field, for example as represented in phantom as 25 in FIG. 2, to extend toward and between adjacent bracketting valleys 19, and to then progress substantially uniformly in a longitudinal direction through the core following the generally convex curvature of fluted surface 15 from platform surface 12 to bottom surface 13.

If the initial fracturing force were permitted to continue in a generally vertical direction, the fracturing vector curve would progressively continue inwardly into the body of core 10 and would result in an implement which would be highly impractical for use in delicate cutting procedures. Accordingly, once vertical implement F has initiated a suitable static stress field in shaped core 10, it will then be required to be shifted outwardly away from face 15 of core material 10, as represented in FIG. 3, to control the direction of fracture by providing a secondary vector of force which proceeds or is directed longitudinally parallel to adjacent ridge 18 of surface 15 of core 10 between bracketting valleys 19.

Figure 5:
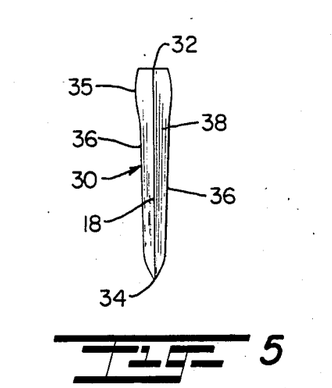
FIG. 5 is a front view in elevation of one preferred form of cutting implement made from the core material shown in FIGS. 2 to 4 in accordance with the method of the present invention.
Figure 6:
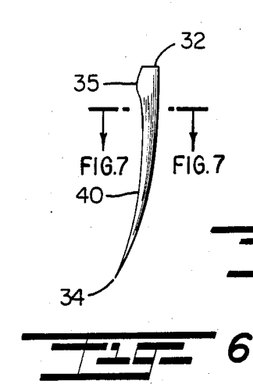
FIG. 6 is a side view in elevation of the cutting implement illustrated in FIG. 5.
Figure 7:
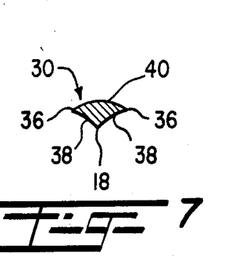
FIG. 7 is a cross-sectional view of the cutting implement of FIGS. 5 and 6 taken along line 7—7 of FIG. 6.

FIGS. 5, 6 and 7 illustrate in somewhat more detail the resulting cutting implement 30 which will be formed using the method of the present invention from a core having the shape of core 10. Cutting implement 30 will be in the form of an elongated slender body having a proximal end 32, formed out of a portion of platform surface 12 of core 10, a distal end 34 at its opposite end with the body tapering from an enlarged bulb of force 35 adjacent to the upper or proximal end 32 downwardly into the tapered distal end 34. Core ridge 18, which will have helped to guide the fracture, will extend medially between opposed lateral cutting edges 36 which will result from the fracture. Cutting edges 36 may have radii of curvature of as little as 30 to about 60 angstroms. Ridge 18 will effectively separate the dorsal surface portions of the blade into a pair of dorsal surface portions 38, each portion 38 being between ridge 18 and a cutting edge 36. Each dorsal portion 38 will have a convex longitudinal curvature from proximal end 32 to distal end 34. Each dorsal portion 38 will also have a concave cross-section across its width between medial ridge 18 and each cutting edge 36. In turn, inner or ventral surface 40 which will be formed by the fracture generated longitudinally from fracture vector curve 25 by implement 30 will have a slightly concave longitudinal configuration from upper bulb of force 35 to lower tapered distal end 34. However, ventral surface 40 will have a convex cross-section across its width between opposed cutting edges 36. As illustrated, upper bulb of force 35 can be seen to take the form of an enlarged or thickened area formed immediately beneath top portion 12 of core 10 at what will have become proximal end 32 of implement 30. Bulb 35 will be so formed as an aspect of the fracturing method of the present invention. The cutting implements thus formed will be suitable for surgery when hafted onto or into a handle.

It will be appreciated that the configuration of front and rear surfaces 15 of core 10 is such that a plurality of cutting implements can be formed out of each surface 15 by proceeding across the face to fracture a cutting implement from the portions centered on each ridge 18 and its pair of bracketting valleys 19. Additionally, it will be further appreciated that once fracturing is completed along one face 15, a series of secondary ridges, not shown, will be formed at what were formerly valleys 19 of original surfaces 15. However, the secondary ridges and valleys formed may not be as sharply defined as those in the original surfaces 15, but nevertheless may be efficiently utilized in the formation of additional cutting elements, thus providing good use of core material 10.

Figures 8, 9, 10, 11, 12, 13:
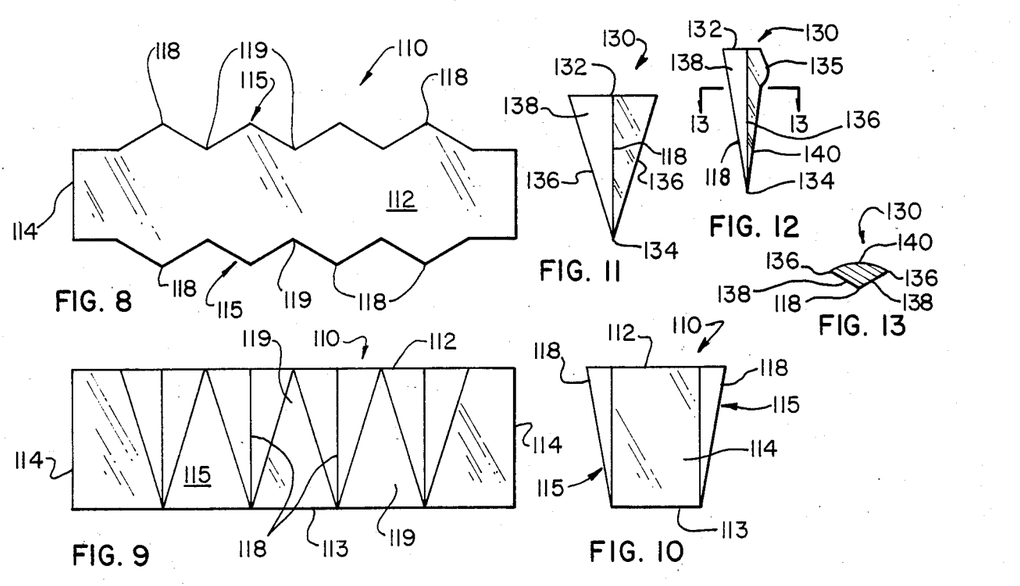
FIG. 8 is a top plan view of another preferred form of preformed core material suitable for use with the methods of the present invention to produce cutting implements.
FIG. 9 is a front view in elevation of the core material shown in FIG. 8.
FIG. 10 is a side view in elevation of the core of FIGS. 8 and 9.
FIG. 11 is a front view in elevation of the cutting implement made from the core material shown in FIGS. 8 to 10.
FIG. 12 is a side view in elevation of the cutting implement illustrated in FIG. 11.
FIG. 13 is a cross-sectional view taken along line 13—13 of the cutting implement illustrated in FIGS. 11 and 12.

Referring now to FIGS. 8 to 13, there is illustrated in detail a method of forming a differently shaped cutting implement from a differently shaped preformed core of material according to the present invention. As in the previous embodiment, the core material 110 will be composed of a vitreous material which is substantially free of structural imperfections, molecular orientations, stress fields, zones of weakness and cleavage, and inclusions, and which will be formed by molding. As in the previous example, core 110 will have flat, sawed top platform surface 112 and bottom surface 113, opposed flat side surfaces 114, and opposed preconfigured front and rear surfaces 115. Front and rear surfaces 115 will carry a plurality of individual jagged or sawtooth discontinuities. As shown in FIGS. 8 to 10, jagged surfaces formed in this embodiment along each surface 115 will be seen to consist of a plurality of parallel relatively sharp-edged ridges 118 extending in the same longitudinal direction from upper platform surface 112 to bottom surface 113. Each ridge 118 will be separated from the next adjacent ridge 118 by a triangular valley 119 having a substantially planar bottom. The profile between the edge of each valley's planar bottom and the adjacent ridges 118 will also be substantially planar.

In the practice of the method of the present invention, core material 110 will again be placed in a holding device, such as a vise, not shown. As in the previous embodiment, a fracturing tool, not shown, will be placed into engagement with top surface 112 of core 110 directly behind a ridge 118. The exact point of engagement will be on the order of the depth of valley 119 and substantially midway between adjacent valleys 119. The initial and primary vector of force which will be exerted on platform surface 112 of core 110 in initiating a fracture in the core material will be in a vertically downward direction or substantially parallel to ridge 118. Once the fracturing static force process has been initiated, the vector or direction of force will be modified by applying a second vector of force so that the direction of the tool applying the force will be nearly normal to and outwardly away from surface 115. Thus, the primary vector of force will first be in a direction parallel to the direction of extension of ridge 118, while a secondary vector of force will then be applied in a direction more nearly perpendicular to and away from the direction of extension of ridge 118. Application of increasing pressure will cause a fracture curve to extend between the edges of the planar portions of adjacent bracketting valleys 119, and to then progress uniformly in a direction following the generally linear direction of ridge 118 from top surface 112 to bottom surface 113.

FIGS. 11 to 13 illustrate in detail the resultant cutting implement 130 formed using the method of the present invention from a core having the shape of core 110. Cutting implement 130 will be in the form of an elongated substantially triangular body having a proximal end 132 formed out of a portion of top platform surface 112 of core 110, a pointed distal end 134 at its opposite end with the body tapering from an enlarged bulb of force 135 adjacent to the upper or proximal ventral end 132 downwardly into the tapered distal end 134. Core ridge 118, which will have guided the fracture, will extend medially between opposed lateral cutting edges 136 which will result from the fracture and effectively separate dorsal surface 138 of the blade intermediately of adjacent valleys 119 into flat portions between ridge 118 and cutting edges 136. Dorsal portion 138 will consist of two surfaces which proceed in a planar fashion downwardly from proximal end 132 to distal end 134, and will have an angle cross-section across its two surfaces which are defined between medial ridge 118 and each opposed cutting edge 136. In turn, the inner or ventral side 140 which will have been formed along the line of fracture of implement 130 will also be of generally linear configuration from upper bulb of force 135 to lower tapered end 134. However, ventral surface 140 will be moderately convex in cross-section between opposed edges 136. The cutting implements so formed will be suitable for surgery.

It will be appreciated that the configuration of front and rear faces 115 of core 110 is such that a plurality of cutting implements 140 can be formed out of each surface by proceeding across the face to fracture a cutting implement from the portions defined by each ridge 118. Additionally, it will be further appreciated that once fracturing is completed along one face 115, a series of secondary ridges will be formed between what were formerly valleys 119 of the primary surfaces 115 or valleys 119. However, the secondary ridges and valleys formed will be concave in cross-section, rather than planar, and will not be as sharply defined as those in the original primary surfaces. Nevertheless, the secondary surfaces thus produced may be utilized in the practice of the method of the present invention for the formation of additional cutting elements, thus providing efficient use of core material 110.

Now, referring to FIGS. 14 to 19, there is illustrated yet another embodiment of the present invention for use in methods of forming cutting implements from yet another preformed core of material 210. Again, core material 210 will be composed of a vitreous material which is substantially free of structural imperfections, molecular orientations, stress fields, zones of weakness and cleavage, and inclusions, and which will be formed and shaped to the configuration shown by molding. Core 210 will have flat top and bottom surfaces 212 and 213, respectively, opposed flat side surfaces 214, and opposed preconfigured front and rear surfaces 215. Front and rear surfaces 215 will carry a plurality of complex yet different individual convex portions, for example 230 and 231. From a consideration of FIG. 14, convex portions 215 formed in this embodiment along each face will be seen to consist of a plurality of initially parallel convex ridges 218 extending initially in substantially the same longitudinal direction, and then curving sideways and tapering from upper surface 212 towards bottom surface 213. Each convex ridge 218 will be separated from the next adjacent ridge 218 by a valley 219 which will be initially parallel and will then correspondingly curve to follow and define the shape of surface portion 215. The shape of portion 215, and the sizing and spacing between the ridges and valleys will largely dictate the shapes and sizes of the cutting implements to be formed from core 210.

In this embodiment, as in the foregoing embodiments, in the practice of the method of the present invention core material 210 will be placed in a conventional holding device. A fracturing tool, not shown, will be placed into engagement with top surface 212 of core 210 directly behind a ridge 218. The exact point of engagement will be substantially midway between adjacent valleys 219.

With this more complex form of starting core material 210, the primary vector of force which will still be exerted on top platform surface 212 of core 210 in initiating a fracture in the core material in a vertically downward direction or substantially parallel to the direction of the top of ridge 218. Once the fracturing process has been so initiated, such as by the application of continuous pressure with a punch, the vector or direction of force will be modified by applying a second vector of force so that the direction of the tool applying the force will be more nearly normal to and outwardly away from the face of portion 215 from which the cutting implement is to be formed. Thus, once again, the primary vector of force will first be in a direction parallel to the initial direction of extension of ridge 218, while a secondary vector of force will then be applied in a direction more nearly transverse to and away from the direction of extension of ridge 218. Application of increasing primary and secondary pressure will cause a fracture line to extend between the bottoms of adjacent bracketting valleys 219, and to then progress uniformly in a direction following the complex curvature of ridge 218 from top platform surface 212 to its termination.

Figures 14, 15, 16, 17:
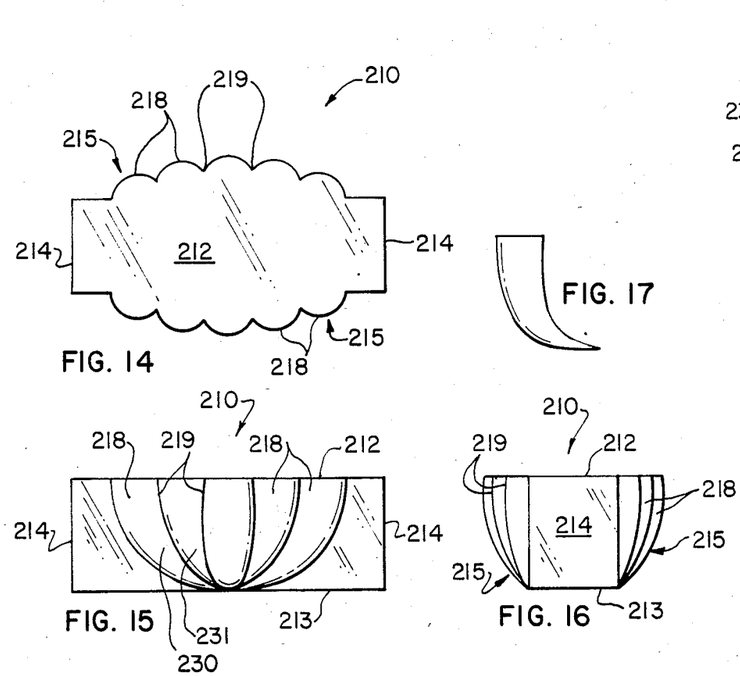
FIG. 14 is a top plan view of yet another form of preformed core material suitable for use with the methods of the present invention to produce cutting implements.
FIG. 15 is a front view in elevation of the core material shown in FIG. 14.
FIG. 16 is a side view in elevation of the core of FIGS. 14 and 15.
FIGS. 17 and 18 are front views in elevation of two differently shaped cutting implements made from the core material shown in FIGS. 14 to 16.

FIGS. 17 to 20 illustrate in somewhat more detail two of the resultant complexly curved cutting implements 230 and 231 formed from core portions 230 and 231, as shown in FIG. 15, using the method of the present invention from a core having the shape of core 210.

Figure 18:
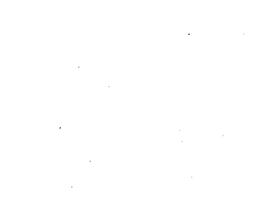
Figure 20:
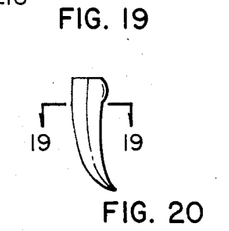
FIG. 20 is a side view in elevation of the cutting implement illustrated in FIGS. 18 and 19.

Each cutting implement 230 and 231 will be in the form of a complexly curved slender body each having a proximal end 232 formed out of a portion of top platform surface 212 of core 210 and a distal end 234 transversely displaced therefrom. Each body will taper from upper or proximal end 232 downwardly into a tapered distal end 234. Core ridges 218 of implements 230 and 231, which will have guided the fracture, will curve both convexly and sideways between opposed lateral cutting edges 236 which will result from the fracture. The sideways curvature will be as shown in FIGS. 17 and 18. The convex curvature is not shown, but will be similar to that shown in FIG. 6. Cutting edges 236 will effectively separate dorsal surfaces 238 from the ventral surfaces 240 of each implement. Dorsal portions 238 will curve transversely and downwardly along a somewhat convex longitudinal line of curvature from proximal end 232 to distal end 234, and will have a convex cross-section across its width between opposed cutting edges 236. In turn, the inner or ventral side 240 which will be formed along the line of fracture of implements 230 and 231 will be of generally concave longitudinal configuration from an upper bulb of force, not shown, to lower tapered end 234, and will also have a convex cross-section across its width between opposed cutting edges 236. Edges 236 will have radii of less than 300 angstroms, and perhaps of as little as about 20 to about 60 angstroms. As such, they are especially useful as surgical scalpels where complexly curved blades are desirable.

It will be appreciated that the configuration of front and rear faces 215 is such that a plurality of differently configured cutting implements can be formed out of each surface by proceeding across the face to fracture a cutting implement from the portions defined by each portion 218.

It is therefore seen that in accordance with the practice of the method of the present invention, cutting implements of various configurations and sizes which are composed of glass or other vitreous material can be formed from core material which is substantially free of structural imperfections, molecular orientations, stress fields, zones of weakness and cleavage, and inclusions which might disrupt the desired and anticipated fracturing of the core.

Preferred embodiments have taught the use of core material which has been molded to a desired shape from hot viscous vitreous material, which core will have at least one ridge or other discontinuity which will define a cleavable portion and configuration. It has been further shown that in the practice of the present invention, by selecting the height of the core, the width and configuration of the ridge or discontinuity, and the point and angle of applied force, the size and configuration of the resulting blade can be substantially predetermined using controlled rate and static force vector pressure fracturing techniques.

It is further seen that in the preferred method of practicing the present invention, static loading force will be applied in fracturing cutting implements from a core of special material. This will be accomplished by applying pressure to the core using a tool which will initially generate stress fields in the core in a cone of about 45° to the platform at which pressure is being applied, followed by the subsequent gradual loading of a second force vector which will cause the stress field to be shifted substantially parallel to the to-be-cleaved surface. It has been taught that such static-loading pressure may be applied in any number of ways, for example with a manual punch or flaking instrument, with a hydraulic press, with a mechanical lever or with other suitable manually manipulated mechanical systems. In preferred embodiments a manually operated machine will be used to exert pressure on the core platform in both the initial and the second vector.

Blades produced by the practice of the method of the present invention are seen to have two intersecting side edges between their dorsal and ventral surfaces. One or both edges will define extremely sharp, uniform, continuous cutting edges, having edge radii usually on the order of about 20 to about 60 angstroms, but almost always less than 300 angstroms, which edges will extend for substantially the entire edge length of the blade body. Typically, such resulting blades will be comprised of a body of elongated slender shape having a proximal or holding end, a distal end and a pair of opposed sharp edges. In certain preferred embodiments, the body of the blade can be made to taper or curve forwardly or sidewardly from the proximal end, and/or terminate in a relatively sharp tapered angle at the distal end. The blades so produced are suitable for even the most delicate surgery, especially after they have been mounted in conventional handles.

As taught, the preferred form of starting core will carry one or more curved or angled ridges which will substantially define the morphology of the resulting implement by directing the fracture path and by defining the lateral width of the resulting blade. In a similar manner, the dorsal surface of the resulting blade will be longitudinally curved or straight between the proximal and distal ends, as was the curve or plane of the core body from which it was fractured. As taught herein, in preferred embodiments a plurality of vitreous cutting blades of substantially the same size, configuration and sharpness can be produced from a single core of starting material. As a result, the method of the present invention provides for the rapid, safe economical manufacture of unique vitreous cutting blades which may be of almost any standard or desired specific size and configuration, and of sharpness especially suitable for even the most delicate surgical procedures.

Blades so produced will normally be placed in a handle or holder for use as cutting implements. Standard handle, haft or holder technology will be suitable for this purpose.

While amorphous, vitreous glass is the material of choice in the practice of the present invention, any other vitreous or microcrystalline material which can be produced as a core of material which is substantially free of structural imperfections, molecular orientations, stress fields, zones of weakness and cleavage, and inclusions can be used in the practice of the methods of the present invention. Where glass is the material of choice almost any existing glass formula including fused mixtures of silicates of alkali, alkaline earth or heavy metals may be suitable. In many preferred embodiments, colorants such as cobalt oxide, antimony, cuprous oxide, chromium oxide, ferrous sulfate, and others may be beneficially used. Such addition of colorants increases the visibility of the blades, for example for improved visibility when cutting clear or aqueous tissue, such as in eye surgery, and for sharpness-measuring purposes.

Having thus described the invention, it will be understood by those skilled in the art that the foregoing and other modifications or changes in form and details may be made therein without departing from the spirit and scope of the invention as claimed, except as they may be precluded by the prior art.

I claim:

1. The method of producing a cutting implement of predetermined size and configuration composed of vitreous or ceramic material from a preformed solid core of such material, comprising the steps of:
   heating a mass of substantially pure, vitreous or ceramic material to a temperature at which it is in a semiplastic or in a melted state;
   placing said heated mass into a mold which includes at least one indentation to cause the formation in said heated mass of at least one ridge or other protrusion having a specific predetermined morphology;
   while in said mold, cooling said mass uniformly in all directions at a rate calibrated to form a solid core of substantially pure manufactured vitreous or ceramic material which is substantially free of structural imperfections, molecular orientations, stress fields, zones of weakness and cleavage, and inclusions, said solid core including an exterior surface having a first surface shaped by said mold which carries at least one ridge or other protrusion having a specific predetermined morphology;
   forming a second, substantially flat surface on said core at a location angularly adjacent to and intersecting said ridge or other protrusion, carried by said first surface;
   directing fracturing pressure in a controlled direction of force into said core at said flat second surface in the vicinity adjacent to said ridge or protrusion of said first surface and in a direction substantially parallel to the longitudinal direction of said first surface to cause the elastic limit of said core material to be exceeded, whereby a cutting implement having a predetermined size and configuration as substantially defined by the morphology of said ridge or protrusion will be sheared from said core.

2. The method of claim 1, wherein the preformed solid core is composed of vitreous material.

3. The method of claim 2 wherein the application of said fracturing pressure, comprises the steps of:
   directing a first pressure vector in a controlled direction of force into said core at said flat second surface in the vicinity adjacent to said ridge or protrusion of said first surface and in a direction substantially parallel to the longitudinal direction of said first surface to cause the generation of a stress field in said core; and
   then directing a second and additive pressure vector in a controlled direction so as to cause said stress field generated in said core to extend in a direction substantially parallel to said first core surface, whereby when the elastic limit of said core material is exceeded a cutting implement having a configuration substantially defined by the morphology of said adjacent ridge or protrusion will be sheared from said core.

4. The method of claim 3 wherein said flat surface is formed by sawing said core after molding is completed and the core has hardened.

5. The method of claim 3 further including the step of placing said core in a support and holding device prior to the application of pressure vectors thereto.

6. The method of claim 3 wherein said first surface of said preformed core is characterized by having more than one ridge or protrusion each having a specific morphology, in the vicinity of which ridges or protrusions pressure vectors can be applied sequentially, whereby the morphology of each said ridge or discontinuity will substantially define the configuration of the resulting implement so sheared from said core.

7. The method of claim 6 wherein there are a plurality of longitudinal ridges carried by said first surface of said preformed core.

8. The method of claim 7 wherein said ridges are adjacent to one another, are separated by valleys and are initially substantially parallel to one another at the portion of said first surface adjacent said second flat surface.

9. The method of claim 8 wherein said preformed core and said ridges taper inwardly in a longitudinal direction from the portion adjacent said second flat surface.

10. The method of claim 8 wherein said first face of said preformed core, and said ridges carried by said first face curve convexly in the longitudinal direction from the portion adjacent said second flat surface.

11. The method of claim 10 wherein said ridges also curve in a lateral direction.

12. The method of claim 8 wherein said ridges curve in a lateral direction.

* * * * *